United States Patent [19]

Bucovaz et al.

[11] 4,424,278

[45] Jan. 3, 1984

[54] CANCER DETECTION PROCEDURE USING AN ACYL CARRIER PROTEIN

[75] Inventors: Edsel T. Bucovaz; Walter D. Whybrew, both of Memphis, Tenn.

[73] Assignee: Research Corporation, Lexington, N.Y.

[21] Appl. No.: 321,782

[22] Filed: Nov. 16, 1981

[51] Int. Cl.³ ............................................. G01N 33/16
[52] U.S. Cl. ..................................... 436/501; 436/504; 436/64; 436/63; 436/86; 436/813; 424/177; 424/1.1; 260/112 R; 435/23; 435/18; 435/4; 435/68
[58] Field of Search ............................ 424/1, 1.5, 177; 23/230 B, 230 R; 436/501, 504, 63, 64, 86, 813; 260/112 R; 435/4, 18, 23, 68

[56] References Cited

U.S. PATENT DOCUMENTS 4,160,817 7/1979 Bucovaz et al. .......................... 424/1
4,234,476 11/1980 Bucovaz et al. ................. 260/112 R
4,261,967 4/1981 Bucovaz et al. .......................... 424/1
4,368,262 1/1983 Bucovaz et al. ...................... 435/23

FOREIGN PATENT DOCUMENTS 2648458 3/1978 Fed. Rep. of Germany .

OTHER PUBLICATIONS

Bucovaz, E. T. et al., Federation Proceedings, vol. 41, No. 3, abstract 341, (1982).

Primary Examiner—Benjamin R. Padgett
Assistant Examiner—M. Moskowitz
Attorney, Agent, or Firm—Scully, Scott, Murphy and Presser

[57] ABSTRACT

A method of detecting cancer in mammals which comprises admixing with a serum sample from said mammal detectably labelled acyl carrier protein and subsequently determining the amount of B-protein-acyl carrier protein complex which is formed.

22 Claims, No Drawings

CANCER DETECTION PROCEDURE USING AN ACYL CARRIER PROTEIN

BACKGROUND OF THE INVENTION

1. Field of the Invention

The present invention relates to a method of detecting the presence of cancer in a host by analyzing the serum sample for the presence or absence of the Bucovaz (B)-Protein.

2. Description of the Prior Art

U.S. Pat. No. 4,160,817 to Bucovaz et al suggests the possibility of diagnosing the presence of cancer in a host by analyzing a serum sample from the host for the presence or absence of B-protein. The technique disclosed in this patent has proven to be extremely accurate in clinical studies which have been completed to date. Unfortunately, the diagnostic procedure disclosed in 4,160,817 patent is labor intensive and requires a fairly long period of time.

U.S. Pat. No. 4,234,476 to Bucovaz et al is a division with U.S. Pat. No. 4,160,817.

U.S. Pat. No. 4,261,967 and U.S. application Ser. No. 058,143 filed July 17, 1979 disclose an improved reagent for use in the process of U.S. Pat. No. 4,160,817. The use of the improved reagents increased the sensitivity of the diagnostic procedure disclosed in the 4,160,817 Patent but does not reduce either the time or the amount of labor required for the diagnostic procedure.

The present inventors in an application Ser. No.: 246,311 filed Mar. 23, 1981 now U.S. Pat. No. 4,368,262, issued Jan. 11, 1983 entitled "Diagnostic Test for the Detection of Cancer" have disclosed a much quicker and less laboring intensive cancer detection procedure. This procedure is easily automated and can provide for a very quick diagnosis. However, unlike the procedure of the U.S. Pat. No. 4,160,817 this new procedure does not allow the doctor to easily follow the course of cancer treatment.

A further discussion of the state of the art is to be found in U.S. Pat. No. 4,160,817.

Accordingly, there continues to exist a need for an accurate and sensitive test for detecting cancer which is fast and inexpensive.

SUMMARY OF THE INVENTION

An object of the present invention is to provide for a fast and inexpensive test for detecting the presence of cancer in a host animal.

Further object of the present invention is to provide for fast and inexpensive diagnostic test which allows the medical profession to monitor the success or failure of cancer treatment procedures.

Yet a further object to the present invention is to provide a novel reagent for detecting the presence of cancer in a host animal.

These and other objects in the present invention which will become apparent from the following description have been achieved by mixing a serum sample from the host animal with a detectably labeled acyl carrier protein followed by measuring the amount of acyl carrier protein which becomes bound to the proteins in the serum sample and comparing that with known standards obtained from cancerous and noncancer resource host.

DETAILED DESCRIPTION OF THE PREFERRED EMBODIMENT

The present diagnostic procedure is based upon the finding that proteins contained in blood serum samples from a cancerous host are different from the proteins in serum samples from a non-cancerous host. The diagnostic procedure disclosed in the U.S. Pat. No. 4,160,817 relied upon the fact the serum samples from cancer resources denatured to detectably different extent than proteins from a non-cancerous resource. The procedure of our application Ser. No. 246,311 now U.S. Pat. No. 4,368,262, issued Jan. 11, 1983, was based on the further discovery that the precipitated proteins obtained from a cancer resource resolubilized to detectably different extent than did protein precipitated from non-cancer resources. The present diagnostic procedure relies upon the same two findings to allow one to discriminate between cancerous and non-cancerous serum samples.

The present diagnostic procedure relies upon the use of a detectably labeled acyl carrier protein for success. Acyl carrier proteins are found in many substances in nature. The particular source of acyl carrier protein is not critical and it can be derived from any source such as *Escherichia coli* B cells or *E. coli* K 12 UB 1005 disclosed by Rock et al in Analytical Biochemistry 102, pages 362 to 364 (1980). An acyl carrier protein-like material has also been identified as being components of the multi-enzyme complex of yeast fatty-acid-synthetase complex. Any of these sources may be used in the preparation of acyl carrier protein. The only criteria is that the acyl carrier protein be in active form which promotes fatty acid synthesis from acetyl-CoA and malonyl-CoA in the presence of other required components (Prescott, D. J. and Vagelos, P. R., Advances in Enzymology, 31 269 (1972) and conform holo-ACP from apo-ACP and CoA in the presence of phosphopantetheinetransferase. A particularly preferred technique for preparing acyl carrier protein is that described by Rock et al cited previously.

The acyl carrier protein must be labeled in some manner such that its presence can be detected quantitatively and preferably both quantitatively and qualitatively. Essentially any procedure for detectably labeling acyl carrier protein may be employed including both enzymatic and radioactive labeling; see $^{14}C$ labelling of ACP described by Vagelos et al in Federation Proceedings, 25:1485–1494 (1966) and $^{125}I$ labelling of proteins similar to ACP such as the Bolton-Hunter method (Biochem. J., 133:529–539 (1973). Radioactive labeling of the acyl carrier protein using tritium is a particularly preferred technique. Such procedures are well known in the art, see Evans, E. A., "Tritium and its Compounds", 2nd edition, London, Butterworths, 1974, 832 pp.

The use of acyl carrier protein as the detectably labeled material offers a tremendous advantage over the reagents disclosed in the U.S. Pat. No. 4,160,817. With the use of the acyl carrier protein it is possible to produce reagents which from batch to batch contain approximately the same amount of detectable labeling. The reagents disclosed in U.S. Pat. No. 4,160,817 could vary greatly from batch to batch in the amount of detectable label which was included. This meant that for each batch of reagent a new standard necessarily had to be prepared. When using the labeled acyl carrier protein it may not be necessary to prepare a new standard for each batch of reagent.

Serum samples taken from host having cancer contain the proteins normally found in the serum samples from non-cancerous host as well as the B-protein found in host suffering from cancer. From clinical tests performed to date, it would appear that the quantity of normal proteins in the serum taken from host suffering from cancer decreases as the amount of the B-protein increases as the cancerous condition advances. In order to distinguish between cancerous and non cancerous serum samples, it is necessary to treat the serum sample before, simultaneously with or subsequent to the addition of the labeled acyl carrier protein in a manner such that it is possible to discriminate between the B-protein and the proteins normally present in the serum sample by qualitatively determining the relative amount of bound acyl carrier protein which is present. Suitable techniques include discrimination procedure which result in separation of the serum sample, when obtained from cancer resources into B-protein rich phases and B-protein poor phases and when taken from non-cancer resources into protein rich and protein poor phases. Other techniques include complete precipitation of the protein followed by measuring the rate at which the protein resolubilize. As described in U.S. Ser. No. 246,311, now U.S. Pat. No. 4,368,262, issued Jan. 11, 1983, precipitated B-protein resolubilizes at a distinctly different rate than normal protein and provides a basis for discriminating between serum samples from cancerous and non-cancerous sources. As described in the U.S. Pat. No. 4,160,817 B-protein denatures to a different degree than does normal protein contained in serum samples. By using partial denaturization it is possible to obtain from cancerous sources fractions which are rich in B-protein and other fractions which are poor in B-protein. On the other hand, partial denaturization of the serum sample was taken from non-cancerous sources results in protein rich and protein poor phases. When the proteins, both normal and B-protein are labeled with acyl carrier protein it is possible to discriminate between samples which are obtained from cancer sources and samples obtained from non-cancerous sources.

Since the detection procedure is based upon being able to detect the presence of labeled acyl carrier protein, the acyl carrier proteins should be admixed with the serum sample under conditions which allow the acyl carrier protein to bind with the proteins present in the serum sample. In order to provide for more reproduceable results it is suggested that the acyl carrier protein be admixed with the serum sample prior to the serum sample being treated to provide for discrimination between B-protein and the normal proteins contained in the serum sample. However, if desired, the acyl carrier protein maybe added to the sample after such treatments have occurred. Therefore, when the precipitation characteristics of the B-protein and normal proteins are employed to discriminate between these proteins in the serum sample it is desirable to admix the acyl carrier protein with the serum sample prior to precipitation of any protein components.

The serum sample itself is any serum sample in which the B-protein can be detected in cancerous sources. A suitable serum sample source are those recovered from blood. In particular blood serum samples which have been allowed to coagulate and centrifuged to separate the packed cells from the serum. A typical procedure is described in the U.S. Pat. No. 4,160,817. Where the acyl carrier protein has been radioactively labeled it is desirable that the serum should not be extensively hemolyzed, as indicated by a dark red color, because the attendant red color species interferes with the assay by quenching the radioactivity which reduces the sensitivity of the test when radioactively labeled acyl carrier protein is used.

The amount of acyl carrier protein which is added to the serum sample is not critical but need only be sufficient to allow discrimination between serum samples taken from non cancerous and cancerous sources as may be readily determined by routine experimentation. Preferably, from 0.1 to 10.0 mg of acyl carrier protein as determined by the method of Lowry (Lowry, et al, J. Biol. Chem., 193, 265–275 (1951)) per mililiter of serum sample are added. More preferably from 0.3 to 0.6 mg of acyl carrier protein per mililiter serum sample are employed. In general, the acyl carrier protein is a dilute solution in order to facilitate handling. The concentration of acyl carrier protein in the solution is not critical but should not be so large as to result in excessive dilution since the large volumes of liquid must be handled. Typically, the acyl carrier protein be added to the serum sample as a aqueous solution containing from 0.1 to 10.0 mg of acyl carrier protein per milliliter of aqueous solution still more preferably from 0.3 to 0.6 mg/ml.

It is believed that the success of the present test in discriminating between serum samples from cancerous and non-cancerous sources is a result of the different rates at which normal protein and B-protein are denaturized. When the protein is denaturized it precipitates from solution. As a result, depending upon the denaturing or precipitating agent employed, the amount of precipitate will differ when one is testing a serum sample from a cancerous source than from a non-cancerous source. The size of this difference depends upon the type of denaturizing agent or precipicating agent which is employed. In some cases, the denaturing agent may denaturize normal protein at a greater rate than the B-protein in which instance serum samples taken from non-cancerous source will show higher radioactive counts than those taken from cancer. On the other hand, when the denaturizing agent effects the B-Protein to a greater extent than normal protein the amount of radioactivity in the precipitated protein sample will be larger when it is obtained from a cancerous source.

The types of denaturizing agents which can be employed have been described in the U.S. Pat. No. 4,160,817 and in application Ser. No. 246,311, now U.S. Pat. No. 4,368,262, issued Jan. 11, 1983. Any of the denaturizing or precipitating agents described in either the patent or the application can be employed in this diagnostic procedure. Trichloracetic acid is the preferred denaturizing or precipitating agent because of the good discrimination which is obtained between cancerous and non-cancerous samples employing this agent.

The reagents used in this procedure will normally be packaged as a kit with instructions as to use. The instructions will include information concerning the serum sample size to be used with the reagents and the other procedures outlined above. The serum sample size is not critical and need only be large enough to allow for sufficient ACP-protein interaction to an extent sufficient to allow detection to an extent such that discrimination between cancerous and non-cancerous samples may be obtained. Generally from 0.01 to 0.10 ml. of serum per 1.0 ml of reagent are employed, still more perfectly from 0.02 to 0.06 ml of serum per ml. of reagent. The reagent will normally contain from 0.01 to 10.0 mg of ACP per ml of solution still more preferably from 0.02 to 0.04 mg of ACP per ml of solution. The solution may comprise labelled ACP and water only or it may contain buffer and/or another protein source, that is an exogenous protein as described in U.S. patent application Ser. No. 246,311, filed Mar. 23, 1981, now U.S. Pat. No. 4,368,262, issued Jan. 11, 1983. It has been found that the use of an exogenous protein, that is a protein source in addition to the labelled ACP and protein in the serum sample improves the test procedure. The preferred exogenous protein are casein and CoA-SPC, more preferably CoA-SPC. If desired, the test reagent may be packaged in several vials. One vial may contain the labelled ACP, buffer and exogenous protein and the second the precipitating agent when simple heating is not used to cause the precipitation or denaturization. Alternatively, one vial may contain labelled ACP, a second vial buffer, exogenous protein and precipitating agent. Other alternatives include separate vials for each of the labeled ACP, exogenous protein and precipitating agent, with the buffer being present in any one of or all of the vials or, alternatively, in a separate vial. When heating is used to denaturize or precipitate the protein from the serum sample, the precipitating agent will be omitted from the kit.

The decision as to whether to use a chemical precipitating agent or heat should be made based solely on convenience since either will perform adequately in the procedure. When a chemical precipitating agent like trichloroacetic acid is used, the test will be somewhat shorter than when heat is used to precipitate or denaturize the proteins in the serum sample. Because of this, the use of a chemical precipitation agent may be preferred to reduce the total time needed to perform the test.

The types and amounts of buffers to be used in this procedure and in these kits are described in U.S. Pat. No. 4,160,817 and application Ser. No. 246,311, filed Mar. 23, 1981, now U.S. Pat. No. 4,368,262, issued Jan. 11, 1983.

In addition to determining presence of cancer by determining the difference in amount of protein which is denaturized under a particular set of conditions, one can also conduct the test by measuring the rate which the protein resolubilizes. As discussed in the U.S. application Ser. No. 246,311, filed Mar. 23, 1981, now U.S. Pat. No. 4,368,262, issued Jan. 11, 1983, B-Protein and normal protein resolubilize at different rates. This distinction can also be employed in the present procedure. In the present instance, the tagged acyl carrier protein would be employed as the medium through which one measures the rate at which the protein resolubilizes. The test is identical to the preceding test which determines differences in denaturization except that the measurement is made by recovering the precipitated protein and then introducing the precipitate into an aqueous medium and determining how fast it resolubilizes and comparing this with a known standard. Using the acyl carrier protein one would proceed by recovering the precipitated protein and introducing it into an aqueous medium for a known period of time followed by separating the remaining protein from the aqueous medium and then determining the number of counts given off by either the aqueous phase or the remaining precipitate. Either measurement could then be compared to a known standard for cancerous and noncancerous samples. By comparing with the known standard one could determine whether the serum sample came from a cancerous or non-cancerous source. Alternate of methods determined in the rate of resolubilization would include after recovering the precipitated protein from the denaturization or precipitation step, washing the precipitated protein and then measuring the amount of labeled ACP remaining either in the precipitated protein or in the wash water. Once again, comparision with a known standard would allow one to determine the presence or absence of cancer. When using this technique it is necessary to wash the serum sample with a standard quantity of water each time. The amount is not critical but larger quantities of water will result in more detectable differences in the amount of radiation either in the washed precipitate or in the wash water. Typically, from 4 to 12 ml of water are used to wash the protein, preferably about 8 ml.

Obviously the acyl carrier protein either detectably labelled or unlabelled may be used as the exogenous protein in the detection procedure described in application Pat. No. 246,311 filed Mar. 23, 1981, now U.S. Pat. No. 4,368,262, issued Jan. 11, 1983. Any of the techniques described in that application may also be used with the acyl carrier protein to determine the rate of resolubilization.

The amount of precipitating agent which is to be employed is not critical. If one is to measure the relative amounts of protein which are precipitated or denaturized then it is necessary to use less precipitating agent than the stoichiometric quantity necessary to precipitate all of the protein from the serum sample. This is necessary because this test relies upon the fact that the B-protein and normal protein are denaturized or precipitated to different extents when subjected to identical precipitation conditions. So long as a stoiciometric insufficiency of precipitating agent is employed the amount of protein precipitated from this serum sample can be used to determine whether a serum sample is from a cancerous or non-cancerous source. Suitable chemical denaturizing agents include trichloracetic acid, zinc sulfate, acetone, ethanol, methanol and hypochlorite. The amount of denaturizing agent to be used can be easily determined by adding different amounts of reagent to the serum sample and observing the amount of protein denaturized. Suitable amounts of reagents per 0.05 ml of serum are:

2 ml 10% TCA
2 ml 1% $ZnSO_4$
2 ml acetone
2 ml 95% ethanol
2 ml 95% absolute methanol
2 ml 10% $HClO_4$ When employing heat to partially denaturize the serum sample one will heat the serum from 70° to 90° C. more preferably from 75° to 85° C. for from 3 to 10 minutes more preferably from 4 to 6 minutes.

The present test procedure is applicable to both humans and animals in detecting the presence and absence of cancer. In humans it will allow the physician to detect the presence of cancer at very early stages when the probability of successful treatment is very large. Furthermore, the test allows the physician to follow the progress of the treatments by measuring changes in the amount of B-protein present in the individuals blood serum. It is believed that the concentration of B-Protein present in a serum sample may be an indication of the stage to which the cancer has progressed. Therefore, it is considered that reductions in the amount of B-protein which is detected in the serum sample is indicative of the successfulness or lack thereof of the treatments in question.

The test also finds use in the animal forms. In particular, in testing laboratory animals for the presence or absence of cancer when they have been exposed to suspected carcinogens. Quite often laboratory animals such as rats or mice are exposed to suspected carcinogens and are subsequently subjected to expensive biopsies to determine whether or not cancer developed. By taking periodic serum samples one can subject a typical animal population to the effect of a carcinogen for a long period of time and periodically monitor that population for the presence or absence of cancer. At the present time it is necessary to sacrifice selected animals from a population in order to do this. Since the populations must be extremely large for any such test to be statistically accurate the present procedure offers a simplification of the present laboratory procedures for testing suspected carcinogenic materials. The test would obviously have application to veterinary medicine where cancer was suspected in an animal.

Having generally described this invention, a further understanding can be obtained by reference to certain specific examples which are provided herein for purposes of illustration only and are not intended to be limiting unless otherwise specified.

EXAMPLES

EXAMPLE 1

For studies of the B-Protein Assay, two types of reaction mixtures[1] and 3 procedures were employed:
[1]The reaction mixture contains 0.5 ml buffer A (containing 50 mM Tris-acetate, pH 7.2; 10 mM magnesium acetate; 25 mM KCl); with or without 0.05 ml of the partially purified yeast extract containing CoA-SPC; 0.01 ml [$^3$H]-ACP (approximately 5,300 cpm) and water to a total volume of 1 ml. To this mixture, 0.05 ml of serum was added.
[2]CPM=counts per minute.

Filtration times are listed to indicate that the addition of ACP does not interfere with the filtration pattern method for the B-protein Assay, application Ser. No. 246,311, filed Mar. 23, 1981, now U.S. Pat. No. 4,368,262, issued Jan. 11, 1983.

Tables 2 through 4 are included to show that various alterations in either the reaction mixture or procedure can be made and still the assay distinguishes between normal and cancerous serum. Furthermore, note that the conditions used for Tubes 3, 4 of Table 3 and Tubes 1, 2 of Table 4 may prove to be effective methods.

Table 2 shows the results of experiments in which reaction mixture 2 and procedure 2 were investigated. Note that in these experiments, CoA-SPC was omitted from the reaction mixture, and the centrifugation step was also omitted.

Table 3 shows the results of experiments in which reaction mixture 1 and procedure 3 were investigated. CoA-SPC was present. The reactions were terminated at 75° or 85° and TCA was not added before filtration. The radioactivity measurements, which are listed, were made after the discs has been washed four times.

TABLE I

REACTION MIXTURE #1 AND PROCEDURE 1

| TUBE NO. | SERUM TESTED | ADJUSTED RADIOACTIVITY (CPM) | ADJUSTED FILTRATION TIME (MIN.) |
|---|---|---|---|
| 1 | Normal | 574 | 7.5 |
| 2 | Cancer | 893 | 9.8 |
| 3 | Normal | 694 | 8.0 |
| 4 | Cancer | 1236 | 14.0 |
| 5 | Normal | 500 | 6.5 |
| 6 | Cancer | 1537 | 33.9 |
| 7 | Normal | 199 | 6.1 |
| 8 | Cancer | 977 | 10.5 |

| REACTION MIXTURE #1 | REACTION MIXTURE #2 | |
|---|---|---|
| [$^3$H]—ACP (5,300 cpm/0.01 ml)[2] | [$^3$H]—ACP (5,300 cpm/0.01 ml) | |
| CoA—SPC | — | |
| Buffer | Buffer | |
| H$_2$O | H$_2$O | |
| Serum | Serum | |
| PROCEDURE 1 | PROCEDURE 2 | PROCEDURE 3 |
| 1. Incubation o-t | 1. incubation o-t | 1. Incubation o-t |
| 2. Stop reaction at 67–69° for 5 min | 2. — | 2. 75° or 85° for 5 min. |
| 3. Cool 5 min. at 20–23° | 3. — | 3. — |
| 4. Centrifuge for 10 min. at 1,500 × g | 4. — | 4. — |
| 5. Decant supernatant liquid | 5. — | 5. — |
| 6. Cool supernatant liquid 5 min at 20–23° | 6. — | 6. — |
| 7. Add 2 ml 10% TCA | 7. Add 2 ml 10% TCA | 7. — |
| 8. Filter and wash 4 × with 2 ml H$_2$O per wash | 8. Filter and wash 4 × with 2 ml H$_2$O per wash | 8. Filter and wash 4 × with 2 ml H$_2$O per wash |
| 9. Measure filtration rate of 1st wash | 9. Measure filtration rate of 1st wash | 9. Measure filtration rate of 1st wash |
| 10. Dry filters | 10. Dry filters | 10. Dry filter |
| 11. Measure radioactivity | 11. Measure radioactivity | 11. Measure radioactivity |

Table 1 shows assay results using reaction mixture 1 and procedure 1. As these data indicate, [$^3$H]-ACP can be used in place of radioactively labeled binding protein in the B-Protein Assay without sacrificing sensitivity or accuracy.

The presence of CoA-SPC in the reaction mixture appears to enhance the level of bound radioactivity as well as the discrimination between normal and cancerous serum. The function of CoA-SPC in the assay is not understood, particularly since the reaction mixture is not incubated, and most of the CoA-SPC is removed by the heating step; 68° C. in this example.

| 9 | Normal | 500 | 6.5 |
| 10 | Cancer | 960 | 32.2 |
| 11 | Normal | 195 | 5.6 |
| 12 | Cancer | 845 | 21.2 |
| 13 | Normal | 575 | 6.5 |
| 14 | Cancer | 1242 | 10.8 |
| 15 | Normal | 495 | 6.5 |
| 16 | Cancer | 1084 | 14.1 |
| 17 | Normal | 500 | 6.5 |
| 18 | Cancer | 787 | 20.6 |
| 19 | Normal | 500 | 4.9 |
| 20 | Cancer | 1366 | 18.1 |
| 21 | Normal | 500 | 6.5 |
| 22 | Cancer | 1252 | 20.2 |

TABLE 2

REACTION MIXTURE #2 AND PROCEDURE 2

| TUBE NO. | SERUM TESTED | ADJUSTED RADIOACTIVITY (CPM) | ADJUSTED FILTRATION TIME (MIN.) |
|---|---|---|---|
| 1 | Normal | 500 | 6.5 |
| 2 | Cancer | 566 | 11.1 |
| 3 | Normal | 500 | 6.5 |
| 4 | Cancer | 951 | 8.4 |
| 5 | Normal | 433 | 6.7 |
| 6 | Cancer | 533 | 7.8 |
| 7 | Normal | 500 | 6.5 |
| 8 | Cancer | 1333 | 9.3 |

TABLE 3

REACTION MIXTURE #1 AND PROCEDURE 3

| TUBE NO. | SERUM TESTED | ADJUSTED RADIOACTIVITY (CPM) | ADJUSTED FILTRATION TIME (MIN.) | TERMINATION TEMPERATURE[3] |
|---|---|---|---|---|
| 1 | Normal | 500 | 6.5 | 75° |
| 2 | Cancer | 549 | 20.5 | 75° |
| 3 | Normal | 500 | 6.5 | 85° |
| 4 | Cancer | 916 | 17.0 | 85° |

[3] All temperatures are °C.

TABLE 4

REACTION MIXTURE #2 AND PROCEDURE 3

| TUBE NO. | SERUM TESTED | ADJUSTED RADIOACTIVITY (CPM) | ADJUSTED FILTRATION TIME (MIN.) | TERMINATION TEMPERATURE |
|---|---|---|---|---|
| 1 | Normal | 768 | 10.7 | 75° |
| 2 | Cancer | 500 | 6.5 | 75° |
| 3 | Normal | 500 | 6.5 | 85° |
| 4 | Cancer | 532 | 18.4 | 85° |

| ADJUSTED C.P.M. | INTERPRETATION OF RESULTS |
|---|---|
| 100–500 | Low probability of cancer |
| 551–650 | Increasing probability of cancer |
| 651–700 | Equivocal results (follow-up tests) |
| 701–899 | Suspicion of Cancer |
| 900-GREATER | High probability of cancer |
| ADJUSTED FILTRATION RATE (MIN.) | |
| 1.0–8.4 | Low probability of cancer |
| 8.5–8.9 | Equivocal results |
| 9.0-GREATER | High probability of cancer |

COMPARATIVE EXAMPLE

Preparation of [$^{35}$S]-Binding Protein

Reaction Mixture: The reaction mixture contained 4.70 mM disodium ATP, pH 7.2; 0.5 ml buffer A (containing 50 mM Tris-acetate, pH 7.2; 10 mM magnesium acetate; 25 mM KCl); 0.5 mM calcium D-pantothenic acid; 0.10 mM [$^{35}$S]-L-cysteine (approximately 20,000 cpm); 0.05 ml of the purified extract containing CoA-SPC and water to a total volume of 1 ml. The mixture was incubated at 36° for 2 h.

Preparation of [$^3$H]-Binding Protein

Reaction Mixture: The reaction mixture contained 4.7 mM disodium ATP, pH 7.2; 0.5 ml buffer A (containing 50 mM Tris-acetate, pH 7.2, 10 MM magnesium acetate, 25 MM KCl); 1.74 nmoles of [$^3$H]-CoA (43,000 d.p.m.); 0.05 ml of the yeast extract containing CoA-SPC and water to a total volume of 1 ml. The mixture was incubated at 36° for 1 h.

Procedure for either [$^{35}$S]-Binding Protein or [$^3$H]-Binding Protein reaction mixtures described above Following incubation, the reaction was terminated by heating the tube in a water bath at 68° for 5 min. The tube was then cooled to 20°–23°, followed by centrifugation at approximately 2,200 rpm for 5 min in a clinical centrifuge. Most of the yeast protein, with the exception of the radioactively labeled binding protein, was removed as a precipitate.

The supernatant fraction was chromatographed on Sephadex G-75. Chromatography on Sephadex G-75 results in the separation of the radioactively labeled binding protein from either unbound radioactive CoA or L-cysteine.

The chromatography fractions containing the radioactively labeled binding protein were pooled (approx. vol. 60 ml), freeze-dried and then reconstituted by adding 1.2 ml of H$_2$O. The total radioactivity content of the solution was between 2,200 to 2,500 cpm.

B-Protein Assay Procedure using Purified Radioactively Labeled Binding Protein The reaction mixture contained 0.05 ml of the serum to be tested, 0.5 ml of buffer A (containing 50 mM Tris-acetate, pH 7.2, 10 mM magnesium acetate, 25 mM KCl), 0.5 ml of the radioactively labeled binding protein (containing approximately 1,000 cpm).

The reaction mixture was incubated for five minutes at room temperature. Two ml of 10% TCA was added and the resulting protein precipitate containing the radioactively labeled-binding protein B-Protein complex, was recovered by filtration on a millipore filtering apparatus using a vacuum of 1 to 4 mmHg and Whatman No. 3. MM paper disc. The protein precipitate collected on the disc was washed 4 times with approximately 2 ml of water per wash, dried in an oven at 95° and then measured for radioactivity content.

TABLE 5

| SERUM TESTED | $^{35}$S-Binding Protein | $^3$H-Binding Protein | Radioactivity (c.p.m.) | Adjusted Filtration Rate (min) |
|---|---|---|---|---|
| Normal | 0.5 | — | 500 | 6.5 |
| Cancer | 0.5 | — | 733 | 25.3 |
| Normal | — | 0.5 | 500 | 6.5 |
| Cancer | — | 0.5 | 696 | 26.5 |

The results in Table 5 demonstrate that the binding protein may react in a manner similar to the acyl carrier protein. However, there is no known procedure for efficiently recovering the radioactivity labelled binding protein. Further, the use of acyl carrier protein appears to result in a much more sensitive procedure.

EXAMPLE 2

In this example the following Reagents were used:
Reagent #1
[$^3$H]-ACP (5,300 cpm/0.01 ml)—0.01 ml
buffer—0.50 ml
water—0.49 ml
Reagent #2
CoASPC 0.05 ml of reagent 2 and 0.05 ml of serum sample were added to 1 ml of reagent 1. The resulting mixture was heated at 68° C., cooled to 20-23° C., centrifuged and filtered in accordance with procedure 1. The results are set forth in Table 6.

TABLE 6

| TUBE NO. | SERUM TESTED | ADJUSTED RADIOACTIVITY (c.p.m.) | ADJUSTED FILTRATION TIME (MIN) |
|---|---|---|---|
| 1 | Normal | 500 | 6.5 |
| 2 | Cancer | 1279 | 13.9 |
| 3 | Normal | 508 | 6.6 |
| 4 | Cancer | 1589 | 13.3 |
| 5 | Normal | 511 | 6.2 |
| 6 | Cancer | 1743 | 14.6 |

EXAMPLE 3

In this example the following reagents were used:
Reagent #1
[$^3$H]-ACP (5,300 cpm/0.01 ml)—0.01 ml
CoA-SPC—0.05 ml
Water—0.40 ml
Reagent #2
buffer—0.50 ml
water—0.40 ml Reagent 2 and serum sample were added to reagent and the procedure described in Example 2 was then followed. The results are set forth in Table 7.

TABLE 7

| TUBE NO. | SERUM TESTED | ADJUSTED RADIOACTIVITY (c.p.m.) | ADJUSTED FILTRATION (TIME (MIN) |
|---|---|---|---|
| 1 | Normal | 500 | 6.5 |
| 2 | Cancer | 1791 | 11.7 |
| 3 | Normal | 456 | 5.4 |
| 4 | Cancer | 1313 | 10.6 |

TABLE 7-continued

| TUBE NO. | SERUM TESTED | ADJUSTED RADIOACTIVITY (c.p.m.) | ADJUSTED FILTRATION (TIME (MIN) |
|---|---|---|---|
| 5 | Normal | 515 | 5.3 |
| 6 | Cancer | 15522 | 12.9 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of detecting cancer in mammals which comprises admixing with a serum sample from said mammal detectably labelled acyl carrier protein and subsequently determining the amount of B-protein-acyl carrier protein complex which is formed.

2. The method of claim 1, wherein the amount of B-protein-acyl carrier protein complex which is formed is determined by partially denaturing the serum sample and measuring the amount of said complex which has been denatured.

3. The method of claim 2, wherein said serum sample is partially denatured by admixing with a chemical denaturing agent.

4. The method of claim 3 wherein said chemical denaturing agent is trichloroacetic acid.

5. The method of claim 3 or 4 wherein the amount of denaturing agent admixed with said serum sample is insufficient to denature the entire protein content of said sample.

6. The method of claim 2 wherein said partial denaturization is accomplished by heating the serum sample at a temperature and time sufficient to only partially denature said serum sample.

7. The method of claim 1, wherein the amount of B-protein-acyl carrier protein complex which is formed is determined by subjecting the admixture to condition which cause the proteins in the sample to precipitate and then measuring the rate at which the proteins resolubilize.

8. The method of claim 7, wherein said proteins are precipitated by admixing with a chemical precipitating agent.

9. The method of claim 8, wherein said chemical precipitating agent is trichloracetic acid.

10. The method of claim 7, wherein said proteins are precipitated by heating the admixture at a temperature and for a time sufficient to cause at least some of said proteins to precipitate.

11. The method of either claims 1, 2 or 7 wherein an exogenous protein is admixed with said serum sample and detectably labelled acyl carrier protein.

12. The method of claim 11 wherein said exogenous protein is admixed with said serum sample prior to admixing with said detectably labelled acyl carrier protein.

13. The method of claim 11 wherein said exogenous protein is admixed with said serum sample simultaneous with admixing with detectably labelled acyl carrier protein.

14. The method of claim 11, wherein said exogenous protein is admixed with said serum sample subsequent to admixing with said detectably labelled acyl carrier protein.

15. The method of claim 11, wherein said exogenous protein is at least one member selected from CoA-SPC, casein, fibrin, albumin, ribonuclease and peptidase.

16. The method of claim 15, wherein said exogenous protein is CoA-SPC.

17. A kit for detection of cancer comprising in combination a vial containing a protein precipitating agent, a second vial containing exogenous protein and a third vial containing detectably labelled acyl carrier protein.

18. The kit of claim 17, wherein an instruction sheet detailing the use of the kit to detect cancer is present in combination with said vials.

19. The kit of claim 17 wherein said precipitating agent is trichloroacetic acid and said exogenous protein is CoA-SPC.

20. A kit for the detection of cancer comprising in a combination a vial containing a protein precipitating agent and a second vial containing exogenous protein wherein at least one of said first and second vials contains detectably labelled acyl carrier protein.

21. The kit of claim 20, wherein at least one of said first and second vials contains a buffer.

22. The kit of claim 20 or 21 wherein said protein precipitating agent is trichloroacetic acid and said exogenous protein is CoA-SPC.

* * * * *